United States Patent [19]

Joseph et al.

[11] Patent Number: 5,688,744
[45] Date of Patent: Nov. 18, 1997

[54] ANTIMICROBIAL COMPOUNDS WITH QUICK SPEED OF KILL

[75] Inventors: Rhoda Weber Joseph, Buckingham; Diane Lynn Antes, Richboro; Peter Osei-Gyimah, Horsham, all of Pa.

[73] Assignee: Rohm and Haas Company, Philadelphia, Pa.

[21] Appl. No.: 729,991

[22] Filed: Oct. 11, 1996

[51] Int. Cl.$^6$ .................. A01N 43/36; A01N 43/82
[52] U.S. Cl. ...................... 504/156; 514/360
[58] Field of Search ................ 514/360; 504/156

[56] References Cited

U.S. PATENT DOCUMENTS

| | | | |
|---|---|---|---|
| 3,718,659 | 2/1973 | Bohme et al. | 260/302 R |
| 3,956,303 | 5/1976 | Bullock et al. | 260/306.8 R |
| 4,059,590 | 11/1977 | Moore | 71/90 |
| 4,119,722 | 10/1978 | Moore | 424/270 |

FOREIGN PATENT DOCUMENTS

| | | | |
|---|---|---|---|
| 28 48 221 A1 | 11/1978 | Germany . | |
| 2848221 | 5/1980 | Germany | 514/360 |

*Primary Examiner*—Allen J. Robinson
*Attorney, Agent, or Firm*—Julie J.L. Cheng

[57] ABSTRACT

A method of inhibiting the growth of bacteria and algae in industrial loci using a compound of formula I or II:

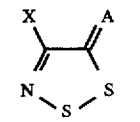

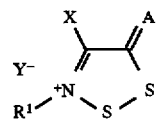

is disclosed. Antimicrobial compounds useful in inhibiting the growth of bacteria and algae in industrial loci and compositions containing the antimicrobial compounds are also disclosed.

3 Claims, No Drawings

ANTIMICROBIAL COMPOUNDS WITH QUICK SPEED OF KILL

This is a nonprovisional application of prior pending provisional application Ser. No. 60/006,244, filed Nov. 3, 1995.

This invention relates to the use of antimicrobial compounds for controlling or inhibiting the growth of microorganisms. In particular, this case relates to the use of dithiazole compounds as antimicrobial compounds.

Antimicrobial compounds are used commercially to control a broad spectrum of microorganisms in various applications.

DE Pat. 28 48 221A assigned to Bayer AG discloses 1,2,3-dithiazol compounds and their use as antimycotic compounds for pharmaceutical use. The patent does not disclose or suggest the use of the compounds for controlling or inhibiting the growth of bacteria or algae in industrial applications. U.S. Pat. No. 4,059,590 (Moore) discloses certain 4-halo-5-aryl-1,2,3-dithiazol compounds and their use as herbicides and fungicides, but does not disclose or suggest the use of such compounds for controlling or inhibiting the growth of bacteria or algae in industrial applications.

A problem with many antimicrobial compounds is that they are slow to kill microorganisms, and/or the compounds persist in the environment. There is currently much concern over adsorbable organic halogens in the environment. There is a need for antimicrobial compounds which do not persist in the environment, have reduced halogen content, and have a quick speed of kill.

The present invention comprises a method of inhibiting the growth of bacteria or algae in industrial loci comprising introducing in, at, or on a locus an effective amount of at least one of an antimicrobial compound of formulas I or II:

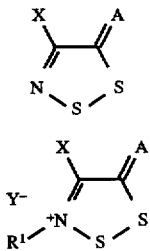

wherein
X and Y are independently selected from Cl, Br, and I;

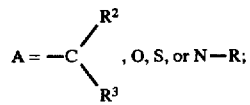

R=phenyl, substituted phenyl, benzyl, methyl, or ethyl;
$R^1 = (C_1-C_8)$ alkyl;
$R^2$ and $R^3$ are independently selected from H, and $(C_1-C_8)$ alkyl.

Another aspect of the invention provides antimicrobial compounds of formula II and compositions further including water and/or water miscible organic solvent.

The compounds according to formula I and II are useful in a number of industrial loci. Suitable industrial loci include, for example, wood, paint, adhesive, caulk, mastic, latex, pulp and paper slurries, textile, leather, plastics, cardboard, lubricants, soaps, cosmetics, detergents, household products, cooling towers, air washers, pulp and paper process waters, metal working fluids, pigment slurries, photographic processing fluids, and fuels. Preferred industrial loci are cooling towers, air washers, pulp and paper process waters, and pigment slurries.

The amounts of compounds according to formula I and II useful to inhibit the growth of bacteria and algae in industrial loci are known to those skilled in the art. Typical amounts are from 0.1 to 2000 ppm based on the locus to be protected. The preferred amount of antimicrobial compound is from 0.1 to 300 ppm, and 1–25 ppm being especially preferred.

By substituted phenyl is meant a phenyl group having one or more of its hydrogens replaced with another substituent group. Examples of suitable substituent groups include $(C_1-C_3)$ alkyl, $(C_1-C_8)$ alkoxy, hydroxy, nitro, halo, cyano, and $(C_1-C_3)$ alkylthio.

As used herein, antimicrobial compounds include bactericides and algaecides and antimicrobial activity is intended to include both the elimination of and inhibition or prevention of growth of microbial organisms such as bacteria and algae in industrial loci.

Preferred antimicrobial compounds for use in this invention include, for example, 4-chloro-5H-1,2,3-dithiazol-5-one; 5-(p-nitrophenylimino)-4-chloro-1,2,3-dithiazole; and 5-(2-chlorophenylimino)-4-chloro-1,2,3-dithiazole.

It is known in the art that the performance of microbicides may be enhanced by combination with one or more other microbicides. Thus, other known microbicides may be combined advantageously with the microbicides of this invention. Microbicides useful in combination with the microbicides of the present invention include, but are not limited to, 5-chloro-2-methyl-3-isothiazolone, 2-methyl-3-isothiazolone, 2,2-dibromo-3-nitrilopropionamide, bromochlorodimethylhydantoin, methylene-bis-thiocyanate, glutaraldehyde, quaternary ammonium compounds, 2-n-octyl-3-isothiazolone, 4,5-dichloro-2-n-octyl-3-isothiazolone, iodopropargyl butylcarbamate, 1,2-dibromo-2,4-dicyanobutane, 2-thiocyanomethylthiobenzothiazole, tetrachloroisophthalonitrile, 5-bromo-5-nitro-1,3-dioxane, 2-bromo-2-nitopropanediol, N,N'-dimethylhydroxyl-5,5'-dimethylhydantoin, 1,2-benzisothiazolin-3-one, and 4,5-trimethylene-2-methyl-3-iosthiazolone. Combinations of the microbicides of the present invention with 5-chloro-2-methyl-3-isothiazolone, 2-methyl-3-isothiazolone, 2,2-dibromo-3-nitrilopropionamide, bromochlorodimethylhydantoin, methylene-bis-thiocyanate, glutaraldehyde, quaternary ammonium compounds and mixtures thereof are preferred.

The following examples are presented to illustrate further various aspects of the present invention, but are not intended to limit the scope of the invention in any aspect.

EXAMPLE 1

Preparation of 4-chloro-5H-1,2,3-dithiazol-5-one

4-Chloro-5H-1,2,3-dithiazol-5-one was prepared according to the process described in DE 28 48 221 A1.

EXAMPLE 2

Preparation of 5-(p-nitrophenylimino)-4-chloro-1,2,3-dithiazole 5-(p-Nitrophenylimino)-4-chloro-1,2,3-dithiazole was prepared according to the process described in DE 28 48 221 A1.

EXAMPLE 3

Preparation of 5-(2-chlorophenylimino)-4-chloro-1,2,3-dithiazole 5-(2-Chlorophenylimino)-4-chloro-1,2,3-dithiazole was prepared according to the process described in DE 28 48 221 A1.

EXAMPLE 4

Antimicrobial Test Data

The spectrum of antimicrobial activity and the effect of anionic surfactant on the antimicrobial activity of the antimicrobial compounds of this invention were determined in minimum inhibitory concentration (MIC) tests. MICs were determined by two fold serial dilutions of a compound in Minimal Salts Media (M9G), Trypticase Soy Broth (TSB) or Tryticase Soy Broth and anionic surfactant (TSB+AOS). The test was performed using a stock solution or dispersion of the test compound, typically at a concentration of 1 percent by weight ("% wt"), made in a 5:3:2 solvent solution of acetone, methanol, and water. A volume of the stock solution was dispensed into culture media to give an initial starting test concentration of 500 ppm compound.

When the test was ready to be done, each vessel in the dilution series, except the first vessel, contained an equal volume of compound free broth. The first vessel contained twice the volume of broth with the starting concentration of test compound. One half of the broth from the first vessel was transferred to the second vessel. After being mixed, one half the resulting volume was removed from the second vessel and transferred to the third vessel. The entire cycle was repeated sufficiently to give a series of concentrations amounting to 500, 250, 125, 63, 31, 16, 8, and 4, 2, 1, 0.5, 0.25 ppm respectively.

Each vessel was then inoculated with a cell suspension of the appropriate test organism. The test organisms and their sources are identified below in Table 1.

TABLE 1

| Organism | Source |
| --- | --- |
| Escherichia coli | ATCC 11229 |
| Rhodotorula rubra | R + H 156 (isolate from contaminated emulsion) |
| Pseudomonas aeruginosa | ATCC 15442 |
| Aspergillus niger | ATCC 6275 |

Bacteria were grown in broth, fungi on agar slants for a time and at a temperature appropriate to the species being tested, and algae were a mixture of green algae and blue-green bacteria grown in a nutrient media. At the end of the growth period, in the case of bacteria, the broth was vortexed to disperse the cells.

In the case of fungi, the spores were harvested by pipetting water onto the slant and dislodging the spores with a sterile loop. The cell/spore suspension was standardized by controlling incubation time, temperature, and the volume of the diluent. The suspension was then used to inoculate the vessels containing the broth compound.

The vessels were then incubated at the appropriate temperature. After the incubation, the vessels were examined for growth/no growth. The minimum inhibitory concentration (MIC) is defined as the lowest concentration of compound that results in complete inhibition of growth of the test organism. Results of the MIC test are shown below in Table 2.

TABLE 2

Minimum Inhibitory Concentration (ppm)

| Compound | E. Coli M9G | E. Coli TSB | P. aeruginosa TSB | A. niger TSB | R. Rubra TSB | E. coli TSBA |
| --- | --- | --- | --- | --- | --- | --- |
| 1 | 19 | >300 | 125 | 75 | 7.5 | 300 |
| 2 | 250 | 500 | 500 | 50 | 50 | 500 |
| 3 | 32 | 500 | 500 | 50 | 50 | 500 |

EXAMPLE 5

Minimum Inhibitory Concentrations Against Algae

The MICs against algae were determined by the same procedure as the previous test, except the volume of the stock solution dispensed into culture media was enough to give an initial starting test concentration of 25 ppm compound. The test organisms and their sources are listed in Table 3. Results of the MIC tests are shown in Table 4.

TABLE 3

| Organism | Source (UTEX#) |
| --- | --- |
| Chlorella pyrenoidosa | 1230 |
| Scenedesmus quadricauda | 614 |
| Anabaena flos-aquae | 426 |
| Phormidium luridum var olivace | 584 |

TABLE 4

Minimum Inhibitory Concentration (ppm)

| Compound | Chlorella | Scenedesmus | Anabaena | Phormidium |
| --- | --- | --- | --- | --- |
| 4-Chloro-5H-1,2,3-dithiazol-5-one | 3.9 | 3.9 | 3.9 | 7.8 |

From these data, it can be seen that 4-chloro-5H-1,2,3-dithiazol-5-one inhibits algae growth at low levels.

EXAMPLE 6

Speed of Kill

The speed of kill of the compounds of the invention was determined in synthetic cooling tower water ("SCW") according to the following procedure.

TSB medium was prepared by weighing 30 g of TSB into a 2 L flask, adding 1 L of deionized water, and swirling the flask until the TSB was completely dissoved. The medium was then autoclaved at 121° C. for 20 minutes.

A nutrient stock solution was prepared by weighing the following into a 2 L flask: 5.28 g of ammonium nitrate, 2.08 g of anhydrous potassium phosphate, 4.62 g of dextrose, 21.50 g of sodium carbonate, and 20.10 g of potassium sulfate. The total volume was adjusted up to 1 L with water. The solution was filter sterilized and stored at room temperature.

A hardness stock was prepared by weighing the following into a 2 L flask: 59.36 g of calcium chloride (dihydrate), 45.02 g of magnesium chloride (hexahydrate), 0.18 g of ferric chloride (hexahydrate), and 0.24 g of ethylenediaminetetraacetic acid. The total volume was adjusted up to 1 L with water. The solution was filter sterilized and stored at room temperature.

A concentrated corrosion/scale inhibitor stock was prepared by weighing into a 2 L flask: 238.5 g of deionized water, 125.0 g of a 45% wt aqueous solution of potassium hydroxide, 23.0 g of a 49.5–51% wt aqueous solution of sodium tolytriazole, 63.5 g of a 42–44% wt aqueous acrylic polymer, and 50.0 g of an approximately 50% wt aqueous solution of 2-phosphono-1,2,4-butanetricarboxylic acid. The flask was swirled until all liquids were dissolved, and then the solution was filter sterilized and stored at room temperature.

The concentrated corrosion/scale inhibitor stock solution was used to prepare a corrosion/scale inhibitor stock solution by adding 9.20 mL of the concentrated corrosion/scale inhibitor stock solution to a 2 L flask, and adjusting the volume up to 1 L with water, with swirling. The resultant corrosion/scale inhibitor stock solution was filter sterilized and stored at room temperature.

SCW was prepared by adding 900 mL of deionized water and 10.88 mL of the nutrient stock (pH 10–13) into a 2 L flask. The pH was adjusted down to pH 6, then 10.88 mL of the hardness stock was added. This was followed by addition of 10.88 mL of the corrosion/scale inhibitor stock. The pH was then adjusted to 8.5 and the final volume adjusted to 1 L with deionized water. This final solution was filter sterilized and stored at room temperature.

Enriched synthetic cooling water ("ESCW") was prepared by adding dextrose and yeast extract for a final concentration of 3000 mg/L and 1000 mg/L respectively.

Stock cultures of the bacteria to be tested were prepared by inoculating TSB agar plates with a loopful of culture from freezer bacteria stock cultures. Each plate was streaked with only one bacterium. The plates were then incubated at 30° C. overnight, sealed, and placed in a refrigerator until needed (up to one month). The following organsims were used to create the stock cultures.

| | |
|---|---|
| *Pseudomonas aeruginosa* | ATCC 15442 |
| *Klebsiella pneumonia* | ATCC 13883 |
| *Enterobacter aerogenes* | ATCC 13048 |

The inocula were prepared by transferring, by means of an inoculating loop, one bacterium colony from the refrigerated stock cultures to 50 mL of ESCW in a 125 mL Erlenmeyer flask. The flask was placed on a heated (30° C.) shaker overnight. The culture was then adjusted to 0.3 optical density units ("OD") at 660 nm, which gives $10^8$ colony forming units ("CFU")/mL. If necessary, the concentration of the inocula is adjusted by adding SCW. Once an inoculum of each bacteria culture was adjusted to 0.30 OD at 660 nm, the three inocula were combined to make a 1:1:1 mixed inoculum of the three bacteria tested.

Stock solutions of each antimicrobial compound tested were prepared as a 1% wt solution in DMSO. The antimicrobial compounds tested were 4-chloro-5H- 1,2,3-dithiazol-5-one ("invention") and methylene bisthiocyanate ("comparative"), a known commercial antimicrobial compound.

The test samples were prepared as follows. To each of eight 125 mL Erlenmeyer flasks, labeled 1 to 8, were added 49.5 mL of SCW. Sample 1 contains only the SCW and is the blank. To samples 2 to 8 is added 0.5 mL of the mixed bacteria inoculum. Sample 2 contains only the SCW and the inoculum and is the untreated control. Samples 3 to 8 are dosed with either the compound of the invention or the comparative compound. Prior to dosing, the volume that will be dosed is removed from each flask in order to maintain the final volume at 50 mL. Samples 3 to 5 are dosed with 1, 5, and 10 ppm of 4-chloro-5H-1,2,3-dithiazol-5-one respectively. Samples 6 to 8 are dosed with 1, 5, and 10 ppm of methylene bisthiocyanate, respectively. A 2 mL aliquot of both the blank and untreated control was removed as the time zero point. All samples were then placed on a shaker at 35° C.

Aliquots of each sample were taken at 1, 3, 6, 24 and 48 hours. Each aliquot was used to inoculate a microtiter plate containing TSB, using a ten-fold serial dilution. Each plate was incubated at 30° C. for 48 hours. Each plate was then read for growth. The number of wells showing growth was entered into a computer program that calculates the most probable number ("MPN") of CFU/mL. A 3 log reduction of CFU/mL after 6 hours, as compared to the untreated control, is considered a quick speed of kill. The data are shown below.

| | Log of MPN of CFU/mL | | | | | |
|---|---|---|---|---|---|---|
| Sample | Antimicrobial Compound | 0 Hrs | 1 Hrs | 3 Hrs | 6 Hrs | 24 Hrs |
| 1 | blank | <1.11 | <1.11 | <1.11 | <1.11 | <1.11 |
| 2 | untreated control | 6.26 | 6.67 | 6.76 | 7.81 | 7.49 |
| 3 | invention (1 ppm) | — | 6.76 | 6.76 | 6.26 | 8.06 |
| 4 | invention (5 ppm) | — | 3.49 | <1.11 | <1.11 | 4.06 |
| 5 | invention (10 ppm) | — | 2.06 | <1.11 | <1.11 | 2.06 |
| 6 | comparative (1 ppm) | — | 6.67 | 6.49 | 5.76 | 4.49 |
| 7 | comparative (5 ppm) | — | 6.26 | 6.76 | 5.49 | <1.11 |
| 8 | comparative (10 ppm) | — | 6.44 | 6.49 | 5.26 | <1.11 |

These data indicate that 5 and 10 ppm of 4-chloro-5H-1,2,3-dithiazol-5-one are efective at 1 hour whereas 10 ppm of methylene bisthiocyanate, a known commercial antimicrobial compound, is not effective until 24 hours.

What is claimed is:

1. A method of inhibiting the growth of bacteria or algae in an industrial locus comprising introducing in, at, or on said locus an effective amount of at least one of a quick speed of kill, non-environmentally persisting antimicrobial compound of formulas I or II:

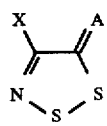

I

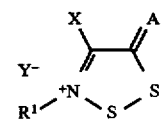

II wherein

X and Y are independently selected from Cl, Br, and I;

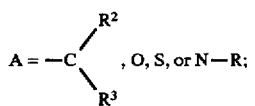

R=phenyl, substituted phenyl, benzyl, methyl, or ethyl;
$R^1 = (C_1-C_8)$ alkyl;
$R^2$ and $R^3$ are independently selected from H, and $(C_1-C_8)$ alkyl.

2. The method according to claim 1 wherein said effective amount of said antimicrobial compound is from 0.1 to 300 ppm based on the total weight of said industrial locus.

3. The method according to claim 1 wherein said industrial locus is selected from the group consisting of wood, paint, adhesive, caulk, mastic, latex, pulp and paper slurries, textile, leather, plastics, cardboard, lubricants, soaps, cosmetics, detergents, household products, industrial cooling water, metal working fluid, pigment slurries, photographic processing fluids, and fuels.

* * * * *